United States Patent [19]

Calini et al.

[11] Patent Number: 4,973,716
[45] Date of Patent: Nov. 27, 1990

[54] PROCESS FOR PREPARING PERFLUOROETHERS BY FLUORINATION WITH ELEMENTAL FLUORINE

[75] Inventors: Pierangelo Calini, Rho; Silvana Modena, Monza, both of Italy

[73] Assignee: Ausimont S.p.A., Italy

[21] Appl. No.: 449,340

[22] Filed: Dec. 11, 1989

Related U.S. Application Data

[63] Continuation of Ser. No. 120,651, Nov. 16, 1987, abandoned.

[30] Foreign Application Priority Data

Nov. 21, 1986 [IT] Italy .................. 22420 A/86

[51] Int. Cl.$^5$ ............................ C07D 307/04
[52] U.S. Cl. .................... 549/504; 549/428; 549/455; 549/511; 549/563; 568/615; 568/683; 568/684; 568/677
[58] Field of Search ............ 549/428, 455, 504, 511, 549/563; 568/615, 677, 683, 684

[56] References Cited

U.S. PATENT DOCUMENTS

| | | | |
|---|---|---|---|
| 3,679,709 | 7/1972 | Frick et al. | 549/504 |
| 3,897,502 | 7/1975 | Russell et al. | 549/455 |
| 4,287,124 | 9/1981 | Siegemund et al. | 549/455 |
| 4,330,475 | 5/1982 | Adcock et al. | |
| 4,523,039 | 7/1985 | Logow et al. | 568/683 |
| 4,684,452 | 8/1987 | Marchionni et al. | |
| 4,686,024 | 8/1987 | Scherer et al. | 568/677 |
| 4,736,045 | 4/1988 | Drakesmith et al. | |
| 4,755,567 | 7/1988 | Bierschenk et al. | 568/615 |
| 4,760,198 | 7/1988 | Bierschenk et al. | 568/615 |

FOREIGN PATENT DOCUMENTS 0269029 6/1988 European Pat. Off. ............ 568/683

*Primary Examiner*—Asok Pal
*Attorney, Agent, or Firm*—Morgan & Finnegan

[57] ABSTRACT

A process for fluorinating hydrogenated ethereal compounds by direct reaction with elemental $F_2$ diluted with an inert gas, wherein the starting compound is in the liquid phase, said fluorination being carried out in the presence of a per fluoropolyetheral compound and of an alkaline metal fluoride.

7 Claims, No Drawings

PROCESS FOR PREPARING PERFLUOROETHERS BY FLUORINATION WITH ELEMENTAL FLUORINE

This application is a continuation of application Ser. No. 120,651, filed Nov. 16, 1987, now abandoned.

DESCRIPTION OF THE INVENTION

The present invention relates to the preparation of perfluorethers starting from the corresponding hydrogenated compounds by fluorination with elemental fluorine conducted in the presence of a perfluoropolyether and of a fluoride of an alkaline metal.

Processes for fluorinating hydrogenated compounds with elemental fluorine are well-known in the State of the Art.

For example, the article by J. L. Adcock and H. L. Cherry in J. Fluorine Inor., 1985, 30 (3) 343, describes the preparation of perfluoroglymes such as perfluorotetramethylenglycol dimethylether by direct fluorination in aerosol. Only 15–36% of the desired product is obtained owing to fragmentation or incomplete reaction.

The article by R. D. Chambers and B. Grierson in J. Fluorine Chem., 1385, 29, 323, describes the fluorination of ethers by means of $CoF_3$ at 400° C. with yields up to 70%.

Such synthesis requires the use of particularly sophisticated apparatus capable of resisting both to the fluorine utilized for preparing $CoF_3$, which is reduced during the synthesis, and to the high temperatures which are usually necessary to the fluorination process. Furthermore, as the reaction proceeds, there is a tendency to lose the halogen different from fluorine.

The article by J. L. Margrave and R. J. Lagow in Prog. Inorg. Chem., 1979, 26, 161, describes the fluorination of ethers through the La Mar process, whereby perfluoroethers are obtained with yields up to 60%.

Such direct fluorination process is carried out at very low temperatures, at least in the first reaction steps.

In order to have a complete fluorination it is then necessary to operate at higher temperature, what requires the use of a plurality of reactors operating at different temperatures.

The article by W. H. Lin, W. I. Bailey, Sr. and M. S. Lagow in chem. Soc. Chem. Commun. 1985, 1350, describes the fluorination, through the La Mar process, of crown ethers by using NaF as a HF captor.

However, the yields obtainable by this process are very low, about 30% of the product to be obtained.

The article by C. Bliefert et al in Kunstoffe 76 (1986) pages 235–240 describes a surface treatment of polymeric (Polyethylene, PPE) articles, powders or foils with elemental fluorine dissolved in either perfluoropolyether compounds or halogenated hydrocarbons.

Owing to this treatment, partially fluorinated surface containing also free radicals is obtained.

It has unexpectedly been found that according to the process of the invention, the fluorination occurs directly, in a single step, without using $CoF_3$, with high yields of thoroughly fluorinated compounds, free from by-products due to the absence of scission reactions and furthermore, starting from hydrogenated chlorine-containing products it is possible to have a selective fluorination avoiding the substitution of the chlorine atoms.

Such processes, moreover, is easily utilizable on an industrial scale, other than the La Mar process with metal fluorides.

The invention relates to the preparation of compounds having general formula:

where:

$R_1$ = perfluoroalkyl containing from 1 to 10 carbon atoms or perfluoroalkylether containing from 2 to 10 carbon atoms;

$R_2$, $R_3$ equal to or different from each other, may be fluorine or perfluoroalkyl containing from 1 to 10 carbon atoms or perfluoroalkylether containing from 2 to 10 carbon atoms;

$R_4$ fluorine or fluoroalkyl containing from 2 to 10 carbon atoms, optionally containing halogen atoms other than F, in particular chlorine;

$R_1$ and $R_2$ can also form together a divalent perfluoroalkyl radical containing from 2 to 10 carbon atoms, optionally comprising 1 to 2 oxygen atoms in the chain.

Said perfluoroethers are obtainable through the process of the present invention by fluorination of hydrogenated compounds such as for example:

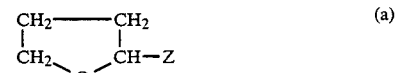

$Z = -CHCl-CH_2Cl, -CH_2-CH_2-CH_3, -CFCl-CHFCl$ $-CH_2-CH_2-OR$, where R is an alkyl with 1 to 3 C,

where Z is the same as defined above.

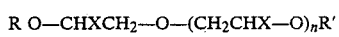

where R and R' are alkyl with 1 to 3 carbon atoms, X is H or $CH_3$ and n is an integer from 1 to 3.

The process of the present invention consists in feeding gaseous $F_2$ diluted with an inert gas in a liquid phase consisting of a perfluoropolyether containing the starting product and an alkaline fluoride.

$F_2$ is generally present in an amount of 20–30% with respect to the inert gas, which preferably is $N_2$ or argon.

The alkaline fluoride, preferably KF, is present in a dispersed form in an amount from 1 to 10 moles (preferably from 2 to 5 moles) for each hydrogen atoms of the starting product which is substituted by fluorine.

The process for preparing the perfluorinated ethers of the above-mentioned classes can be carried out also starting from compounds containing chlorine, which is not substituted by fluorine in the reaction.

The perfluoropolyethers utilizable as a solvent for the process according to the invention must have a boiling point which is higher than the reaction temperature and they can be selected from the ones composed of sequences of one or more oxyperflyoroalkylene units selected from:

$-CF_2O-$; $-CF_2-CF_2O-$; $-CFO-$; $-CF-CF_2O-$;
                                    |          |
                                    CF_3       CF_3

$-CF_2CF_2CF_2O-$;

and having perfluoroalkyl groups as end groups.

Suitable commercial products are those designated by trade-marks Fomblin®, Galden®, Krytox®, Demnum® produced by Daikin.

The process temperature ranges from 20° C. to 150° C., preferably from 40° to 110° C.

The products obtainable through the fluorination process according to the invention are free from incompletely fluorinated compounds and, as is known for the perfluorinated compounds, said products are endowed with an exceptional combination of excellent properties, which make them suitable for a bread range of uses in many industry sectors.

The main characteristics are chemical inertia, thermal stability, uninflammability, high electrical resistivity, low surface tension, low water-solubility, compatibility with many materials such as elastomers and plastomers.

Furthermore, the process for the present invention does not give tise to scission reactions with consequent secondary reactions, wherefore the individual compounds are obtained in a pure state, with well defined boiling points and other physical properties.

Thanks to the above-cited characteristics, the perfluoroethers obtainable by the process according to the invention are particularly suitable for the tests in the field of electronics, such as the thermal shock test, or in operations such as vapor phase soldering or vapor phase curing.

The following examples are given for merely illustrative purposes and are not to be construed as being limitative of the possible embodiments of the present invention.

EXAMPLE 1

Into a glass reactor equipped with a stirrer there were charged 412 g of Fomblin® Y04 and 100 g of finely powdered KF. The solution was heated to 100° C. whereafter, by means of a dipped pipe, a mixture of 3 nl/h of $F_2$ and of 3 Nl/h of $N_2$ was sent into the reactor. The solution was allowed to saturate and then $$\underset{O}{\boxed{\phantom{xx}}}\text{CFCl—CFClH}$$

was fed at a rate of 1 ml/h for 9 hours.

The gases leaving the reactor were collected in a trap cooled down to $-78°$ C. On conclusion of the reaction, 10.3 g (yield=52%) of perfluorinated product characterized by a boiling point of 108° C. were obtained. The $^{14}F$ NMR spectrum was in accordance with the compound of formula:

$$\begin{array}{c} CF_2\text{———}CF_2 \\ |\phantom{xxxx}| \\ CF_2\diagdown\phantom{xx}CF-CFCl-CF_2Cl \\ \phantom{xxx}O \end{array}$$

In fact, the chemical shifts referred to $CFCl_3$ were as follows:

(A) $-CF_2-Cl$ from $-60$ to $-64$ ppm (B) $-CF_2O$ from $-80$ to $-85$ ppm (C) $-CF_2$, CF, CFCl many signals from $-112$ to $-138$ ppm.

The corresponding intensities were in the following ratio: A:B:C=2:2:6.

EXAMPLE 2

The reactor of Example 1 was charged with 400 g of Fomblin Y04 and 100 g of finely powdered KF. The solution was heated to 100° C. whereafter by means of a dipped pipe a mixture of 3 Nl/h of fluorine and $N_2$ was sent into the reactor.

The solution was allowed to saturate and diglyme was introduced at a rate of 0.38 ml/h for 6 hours.

Then in the cooled trap of Example 1, 4.6 g of reaction products were collected.

Said reaction products from GLC analysis contained 76% of a compound which according to $^{19}F$ NMR had the following formula:

$$\overset{a}{CF_3}O\overset{b}{CF_2}-\overset{c}{CF_2}OCF_2-CF_2-OCF_3$$

$$\overset{a}{CF_3} = 55 \text{ ppm}$$

$$\overset{b}{CF_2} = 90 \text{ ppm}$$

$$\overset{c}{CF_2} = 88 \text{ ppm.}$$

The yield of this product was of 56%. The perfluorinated diglyme has the following boiling point: 66° C.

EXAMPLE 3

The reactor of Example 1 was charged with 400 g of Fomblin Y04 and 100 g of KF. Then the temperature was raised to 120° C. and by means of a dipped bipe a mixture of 3 Nl/h of fluorine and $N_2$ gas introduced into the reactor the solution was allowed to saturate and tetraglyme was introduced into the reactor at a rate of 0.38 ml/h for 6 hours.

Then 3.7 g of reaction products were collected into the cooled trap of Example 1 these products contained 75% of a compound which according to $^{19}F$ NMR spectroscopy was in accordance with the following formula:

$$\overset{a}{CF_3}O\overset{b}{CF_2}\overset{c}{CF_2}-O(CF_2-CF_2O)_4CF_3$$

$$\overset{a}{CF_3} = 60 \text{ ppm}$$

$$\overset{b}{CF_2} = 105 \text{ ppm}$$

$$\overset{c}{CF_2} = 103 \text{ ppm.}$$

The yield of this product was 44% and its boiling point 138° C.

EXAMPLE 4

The reactor of Example 1 was charged with 400 g of Fomblin Y04 and 100 g of KF, then the temperature was raised to 100° C. and a mixture of 3 Nl/h of $N_2$ and $F_2$ was sent into the reactor. The solution was allowed to saturate.

Then $$\underset{O}{\overset{O}{\square}}\diagdown CFCl-CFClH$$

was introduced at a rate of 0.95 ml/h. After 6.5 hours 13.4 g of reaction product were collected in the cooled trap of Example 1 containing 80% of a compound having a boiling point of 125° C. and according to $^{19}$F NMR had the following formula:

$$\overset{e}{\underset{f}{\square}}\overset{O}{\underset{O}{\diagdown}}\overset{d}{\underset{c}{\diagdown}}\overset{b}{CFCl}-\overset{a}{CF_2Cl}$$

$\overset{a}{CF_2}$: 64–68 ppm $\overset{b,c}{CF_2}$: 126–136 ppm $\overset{d,e,f}{CF_2}$: 80–98 ppm.

The yield of this product was 74%.

What we claim is:

1. A process for preparing compounds having general formula:

$$R_4-\underset{R_3}{\overset{R_2}{\underset{|}{C}}}-OR_1$$

wherein:

R$_1$ is a perfluoroalkyl containing 1 to 10 carbon atoms or an perfluoroalkylether containing 2 to 10 carbon atoms:

R$_2$ and R$_3$ either equal to or different from each other, can be fluorine or perfluoroalkyl containing 1 to 10 carbon atoms or perfluoroalkylether containing 2 to 10 carbon atoms;

R$_4$ is fluorine or fluoroalkyl containing 2 to 10 carbon atoms, either or not containing halogen atoms other than fluorine;

R$_1$ and R$_2$ being susceptible of forming, together, a divalent perfluoroalkyl radical containing 2 carbon atoms, optionally comprising 1 to 2 oxygen atoms in the chain;

comprising reacting elemental fluorine with an at least partially hydrogenated ether compound, in the presence of a reaction solvent consisting of a perfluoropolyether, and of an alkaline metal fluoride in an amount ranging from 1 to 10 moles per hydrogen atom of the starting product, at a temperature ranging from 20° to 150° C.

2. The process according to claim 1, wherein the starting hydrogenated ether product contains also chlorine atoms.

3. The process according to claim 1, wherein elemental fluorine is diluted with an inert gas.

4. The process according to claim 1, wherein the alkaline metal fluoride is KF or NaF.

5. The process according to claim 1, wherein the perfluoroether solvent has a boiling point higher than the reaction temperature and consists of one or more oxyperfluoroalkylene units selected from:

$$-CF_2O-;\ -CF_2-CF_2-O-;\ -\underset{CF_3}{\overset{|}{CF}}-O-;\ -\underset{CF_3}{\overset{|}{CF}}-CF_2O-;$$

$$CF_2CF_2CF_2O-;$$

and having perfluoroalkyl groups as end groups.

6. The process according to claim 1, wherein the temperature ranges from 40° to 110° C.

7. The process according to claim 1, wherein the starting hydrogenated compound belongs to general formula:

$$\begin{array}{c}CH_2\text{------}CH_2\\|\qquad\quad|\\CH_2\qquad CH-Z\\ \diagdown\ /\\O\end{array}$$

wherein Z=—CHCl—CH$_2$Cl, —CH$_2$CH$_2$CH$_3$, —CFCl—CHFCl, —CH$_2$CH$_2$OR. where R is an alkyl with 1 to 3 carbon atoms.

* * * * *